United States Patent
Blank et al.

(10) Patent No.: US 8,672,995 B2
(45) Date of Patent: Mar. 18, 2014

(54) POLYMER PROSTHESIS

(75) Inventors: Thiemo Blank, Bruehl (DE); Thomas Wille, Karlsruhe (DE)

(73) Assignee: C. R. Bard, Inc., Murray Hill, NJ (US)

( * ) Notice: Subject to any disclaimer, the term of this patent is extended or adjusted under 35 U.S.C. 154(b) by 997 days.

(21) Appl. No.: 12/064,233

(22) PCT Filed: Aug. 21, 2006

(86) PCT No.: PCT/EP2006/008217
§ 371 (c)(1),
(2), (4) Date: Aug. 30, 2010

(87) PCT Pub. No.: WO2007/020110
PCT Pub. Date: Feb. 22, 2007

(65) Prior Publication Data
US 2010/0319836 A1    Dec. 23, 2010

(30) Foreign Application Priority Data
Aug. 19, 2005  (GB) .................................. 0517085.7

(51) Int. Cl.
*A61F 2/82* (2013.01)
(52) U.S. Cl.
USPC ...................................................... 623/1.16
(58) Field of Classification Search
USPC .............................................. 623/1.13–1.17
See application file for complete search history.

(56) References Cited

U.S. PATENT DOCUMENTS

| | | | |
|---|---|---|---|
| 4,950,258 A | 8/1990 | Kawai et al. | |
| 5,091,205 A | 2/1992 | Fan | |
| 5,156,620 A | 10/1992 | Pigott | |
| 5,222,949 A | 6/1993 | Kaldany | |
| 5,383,892 A | 1/1995 | Cardon et al. | |
| 5,449,373 A | 9/1995 | Pinchasik et al. | |
| 5,665,114 A * | 9/1997 | Weadock et al. | 623/1.34 |
| 5,873,906 A * | 2/1999 | Lau et al. | 128/898 |
| 6,168,619 B1 * | 1/2001 | Dinh et al. | 623/1.13 |
| 6,554,857 B1 * | 4/2003 | Zilla et al. | 623/1.23 |
| 6,702,802 B1 | 3/2004 | Hancock et al. | |
| 6,899,728 B1 * | 5/2005 | Phillips et al. | 623/1.13 |
| 2001/0021870 A1 | 9/2001 | Edwin et al. | |
| 2002/0178570 A1 | 12/2002 | Sogard et al. | |

(Continued)

FOREIGN PATENT DOCUMENTS

| | | |
|---|---|---|
| EP | 0528181 A1 | 2/1993 |
| EP | 1937184 B1 | 2/2010 |

(Continued)

OTHER PUBLICATIONS

PCT/EP2006/008217 filed Aug. 21, 2006 International Preliminary Report on Patentability dated Feb. 20, 2008.

(Continued)

*Primary Examiner* — Suzette J Gherbi
(74) *Attorney, Agent, or Firm* — Rutan & Tucker, LLP

(57) ABSTRACT

A polymer prosthesis with lumen and an axial length and having in a pre-delivery condition a plurality of relatively stiff stenting segments spaced from each other along the length of the prosthesis, the spaces between the relatively stiff stenting segments of a first polymer being bridged by relatively flexible linking segments of a second polymer, different from the first, the relatively stiff stenting segments and the relatively flexible linking segments being alternately arranged along the length of the prosthesis.

32 Claims, 8 Drawing Sheets

(56) References Cited

U.S. PATENT DOCUMENTS

| | | | |
|---|---|---|---|
| 2003/0055198 A1 | 3/2003 | Langer et al. | |
| 2003/0216804 A1* | 11/2003 | DeBeer et al. | 623/1.15 |
| 2004/0054397 A1* | 3/2004 | Smith et al. | 623/1.13 |
| 2004/0167616 A1* | 8/2004 | Camrud et al. | 623/1.16 |
| 2005/0033399 A1 | 2/2005 | Richter | |
| 2005/0049694 A1* | 3/2005 | Neary | 623/1.46 |
| 2005/0060020 A1* | 3/2005 | Jenson | 623/1.13 |
| 2005/0102022 A1* | 5/2005 | Solovay et al. | 623/1.13 |
| 2005/0107864 A1* | 5/2005 | Hong et al. | 623/1.15 |
| 2005/0125051 A1* | 6/2005 | Eidenschink et al. | 623/1.12 |
| 2005/0143772 A1 | 6/2005 | Burgmeier et al. | |
| 2005/0177222 A1 | 8/2005 | Mead | |
| 2005/0187604 A1* | 8/2005 | Eells et al. | 623/1.13 |
| 2005/0203605 A1* | 9/2005 | Dolan | 623/1.11 |
| 2005/0222667 A1* | 10/2005 | Hunt | 623/1.13 |
| 2005/0267442 A1* | 12/2005 | Von Oepen | 604/509 |
| 2006/0155364 A1* | 7/2006 | Holloway et al. | 623/1.16 |
| 2007/0135889 A1* | 6/2007 | Moore et al. | 623/1.13 |
| 2007/0207186 A1* | 9/2007 | Scanlon et al. | 424/424 |

FOREIGN PATENT DOCUMENTS

| | | |
|---|---|---|
| WO | WO-9526695 A2 | 10/1995 |
| WO | WO-01/21107 | 3/2001 |
| WO | WO-0121101 A1 | 3/2001 |
| WO | 0226279 | 4/2002 |
| WO | WO-03/049641 | 6/2003 |
| WO | WO-03/096934 | 11/2003 |
| WO | WO-2004/110313 | 12/2004 |
| WO | WO-2004/110315 | 12/2004 |
| WO | WO-2005/027792 | 3/2005 |
| WO | WO-2005030092 A2 | 4/2005 |
| WO | 2007020110 A1 | 2/2007 |

OTHER PUBLICATIONS

PCT/EP2006/008217 filed Aug. 21, 2006 Search Report dated Oct. 16, 2006.

PCT/EP2006/008217 filed Aug. 21, 2006 Written Opinion dated Oct. 16, 2006.

* cited by examiner

POLYMER PROSTHESIS

PRIORITY

This application is a United States National Stage Application under 35 U.S.C. §371 of International Patent Application No. PCT/EP2006/008217, filed Aug. 21, 2006, which claims the benefit to United Kingdom Patent Application No. 0517085.7, filed Aug. 19, 2005, each of which is incorporated by reference into this application as if fully set forth herein.

TECHNICAL FIELD

This invention relates to a polymer prosthesis such as a stent, graft or stent-graft, and to a method for making a polymer prosthesis.

BACKGROUND PRIOR ART

WO 03/049641 discloses a cylindrical stent with a longitudinal rotational axis and a plurality of metal stenting rings arranged at spaced intervals along the axis, and carried on an apertured cylindrical polymeric mesh. The polymeric mesh being relatively flexible, the composite stent is comparatively flexible (allowing the stent cylinder to be bendy in the sense that the long axis can easily move from straight to curved configurations) while the metal rings provide a radial strength or force that can push bodily tissue radially outwardly from the lumen of the stent, which strength or force is comparable with conventional metal stents. In this way, one can enjoy the high radial force of a metal stent in combination with the flexibility of polymers to allow the stent to bend with the surrounding bodily tissue.

However, building stents from a composite of metal and polymer requires special production techniques. In implantable prostheses, the task of joining two materials as dissimilar as metal and polymer is one that designers prefer to avoid.

The published patent art is rich in proposals to use shape memory polymers for manufacturing stents. See, for example, WO 2004/110315; WO 2005/027792; WO 03/096934; U.S. Pat. No. 4,950,258; US-A1-2003/0055198 and WO 2004/110313. However, in all of these prior proposals, there is no recognition of various inventive aspects disclosed herein.

SUMMARY OF THE INVENTION

The present invention enables in a prosthesis for transluminal implantation both a high radial strength and high flexibility to allow the prosthesis to bend with flexing and bending of the surrounding bodily tissue.

In one embodiment of the present invention there is provided a polymer prosthesis with an axial length and having in a pre-delivery condition a plurality of relatively stiff stenting segments spaced from each other along the length of the prosthesis, the spaces between the relatively stiff stenting segments of a first polymer being bridged by relatively flexible linking segments of a second polymer, different from the first, the relatively stiff stenting segments and the relatively flexible linking segments being alternatively arranged along the length of the prosthesis. The polymer prosthesis can bend with relatively little flexing of the stenting segments, by means of relatively greater flexing of the linking segments.

The term "alternately arranged" is understood to encompass an arrangement wherein in at least one direction along the length of the prosthesis each relatively stiff stenting segment is followed by a relatively flexible linking segment before the next relatively stiff stenting segment is encountered. Likewise, in at least one direction along the length of the prosthesis each relatively flexible linking segment is followed by a relatively stiff stenting segment before the next relatively flexible linking segment is encountered.

However, within the scope of this term it is possible that between a pair of a relatively flexible linking segment and a closest neighbouring relatively stiff stenting segment, another, different segment is positioned.

The term flexible is understood to encompass bendable without the occurrence of a kink in the bending part. The curvature reachable by a prosthesis according to the invention will depend on the number and dimensions of the flexible linking segments and the extent to which each flexible linking segment is bendable.

The stenting segments can be discrete apertured rings spaced along the length of the prosthesis and, when they are, the linking segments are likely to be discrete rings spaced along the length of the prosthesis. Otherwise, the linking segments can be portions of a continuous annular (e.g. cylindrical) component that extends the full length of the prosthesis and that carries, spaced along the length of that continuous component, the said spaced stenting segments.

The stenting segments could be provided by the successive apertured turns of a spiral or helix, which can run from one end of the prosthesis cylinder to the other. There might be more than one such helical component that provides the stenting segments. The individual turns of the stenting helix are bridged by the linking segments which could themselves be successive turns of one or more helical components.

In one embodiment, the prosthesis is devoid of stenting segments except at its opposite axial ends. The prosthesis serves as an artificial bodily lumen and the stenting segments anchor the two opposite ends of the prosthesis at the desired location in the lumen.

The polymer of the stenting segments are preferably different atomically from the polymer of the linking segments, including stoichiometrically different, although other differences are feasible, such as the respective extent of polymerisation, in other words, the molecular weight of the stenting segments in comparison with the molecular weight of the polymer of the linking segments.

In one embodiment, the polymer of the stenting segments has a glass transition temperature that is greater than body temperature or 37° C. Thus, at body temperature, the polymer of the stenting segments is below its glass transition temperature, and so is comparatively hard. This hardness serves to provide the required relatively high radial strength. For transluminal delivery of the prosthesis to a stenting site, one envisages bringing the prosthesis to the site of the procedure, at a small diameter configuration.

Once the prosthesis is at the desired location, one way to effect the radial expansion is by applying heat to the polymer of the stenting segments in order to raise that temperature to a temperature above body temperature and also above the glass transition temperature of the material. With the material heated above its glass transition temperature, and thereby relatively flexible, a balloon within the lumen of the prosthesis could be inflated (as with conventional balloon-inflatable stainless steel stents) to expand the warmed prosthesis to its final enlarged diameter configuration. At this point, heating would be terminated, to allow the temperature of the radially expanded stenting segments to return to body temperature, which is below the glass transition temperature of the material. In this way, the material or the stenting segments would harden in the enlarged diameter configuration and would in that configuration perform its stenting function.

Another possibility is to build a self-expanding stent and compress it mechanically, radially inwardly, to insert it into a transluminal delivery system for release and self-expansion at the desired location.

Conversely, the polymer that provides the linking segments would likely be one that has a glass transition temperature below body temperature.

Bio-absorbable polymers for building prostheses are known, as such. Suitable bio-absorbable or bio-degradable polymers can be utilized to provide the flexible linking segments and also the harder stenting segments. Examples of suitable polymers are summed up in the section "Detailed description".

In one popular stent graft design, two tubes of expanded PTFE are bonded together at spaced intervals corresponding to apertures between struts of a stent mesh sandwiched between the two tubes. In the present invention, stenting polymer fluid can instead be injected into a pattern defined by local joining together of two concentric ePTFE tubes, with the polymer after injection transforming from a fluid condition to a condition in which it can perform the function of the stenting segments.

In another embodiment, the interstices of an expanded PTFE workpiece, such as an annulus, could be filled with a polymer which provides a stenting function. The filling could take place at intervals along the length of the annulus, to provide the stenting segments of the present invention. Between the stenting segments, the interstices could be left unfilled, filled with another polymer, or used to receive a biologically active compound such as a medicament.

It is thus possible that in an embodiment, the stenting segments occupy a number of selected interstices which are situated within the ePTFE material itself.

The matter to be introduced into the interstices could be borne there in solution, by a solvent that is subsequently removed, for example by evaporation.

In this embodiment, there need be only one annular ePTFE component, not a sandwich of two nested annular ePTFE components.

The following method is suggested for forming a polymer prosthesis with lumen and an axial length. Note that the next three steps of such a method are to be carried out in a pre-delivery stage. The steps comprise:
    providing a plurality of relatively stiff stenting segments of a first polymer;
    providing a plurality of relatively flexible linking segments of a second polymer which are different from the first polymer; and
    bridging relatively stiff stenting segments with a plurality of relatively flexible linking segments.

A large number of embodiments of a method according to the invention is available. It is, for instance, possible that the plurality of relatively flexible linking segments is provided as portions of a continuous cylindrical component of the prosthesis. This in its turn offers the possibility for bridging the relatively stiff stenting segments by attaching each of the relatively stiff stenting segments, or fixedly positioning the relatively stiff stenting segments, to the continuous cylindrical components. Such a method provides a simple and fast way of making the inventive/expanded polymer prosthesis as the linking elements themselves have already been bridged together.

In an embodiment of a method according to the invention is the continuous cylindrical component provided in the form of two concentric tubes bonded to each other by at spaced intervals along the length of the tubes and around their circumference. The reader's attention is drawn to WO 2001/021107 which describes a possible result of such method steps. However, it is to be noted that according to this prior art document an inflatable space between the two concentric tubes is injected with a fluid when the concentric tubes as bonded together are at the delivery side in a body. In contrast, in an embodiment of a method according to the invention will the first polymer which will form at least a part of the plurality of relatively stiff stenting segment be inserted between the concentric tubes while the cylindrical component is still outside the body, i.e. when the component is in a pre-delivery stage. This has the advantage that the making of the polymer prosthesis is very well controllable by the manufacturer of the polymer prosthesis, can be "tailor-made", and for instance be tested before employment.

The cylindrical component may be provided of ePTFE with the stenting segments occupying interstices therein. The ePTFE is normally made separately and preferably in a manner such that interstices are present therein. Such a method is well-known to those skilled in the art. The stenting segments may be formed in those interstices by, for instance, pressing the first polymer into those interstices. However, it is also possible to apply a method of coextrusion. Although interstices may be equally distributed over the ePTFE. It is envisaged that only a selected number of interstices will be occupied with the first polymer, and thus with the stenting segments.

As to other ways of manufacturing the polymer prosthesis or additional information, reference is further made to the published art of making polymer stents, exemplified by the patent publications listed above. Cylindrical strut meshes can be made by moulding, chemical machining of polymer tube and sheet or even weaving of mesh from polymer fibers. One useful way of making the polymer tube or sheet may well be extrusion. However, the ways of forming and machining work pieces of metal are often quite different from the process steps involved in forming working and machining work pieces of synthetic polymeric material. For polymers, such processes as solvent welding could be particularly interesting. For example, one envisages assembling on a cylindrical mandrel a succession of alternate rings of hard and soft polymer, with the successive rings bonded to the adjacent rings if not by an adhesive composition then by heat welding or solvent welding. Alternatively, a spaced succession of hard polymer rings could be cemented, glued, solvent welded or otherwise bonded to the luminal or abluminal surface of a cylindrical component of the soft polymer that runs contiguously for the full length of the prosthesis.

Selection of specific polymers is not of the essence of the present proposal. As indicated above, the published art is replete with discussion of synthetic polymers suitable for making implantable prostheses. The appropriate skilled person will be well able to select from amongst the candidate materials, once informed by the present application of the working principle of the present invention, namely, relatively strong stenting segments capable of pushing bodily tissue radially outwardly, interspersed with relatively soft linking segments that allow a prosthesis as a whole to bend with movements of the bodily tissue in which it is implanted.

BRIEF DESCRIPTION OF THE DRAWINGS

For better understanding of the present invention, and to show more clearly how the same may be carried into effect, reference will now be made, by way of example, to the accompanying drawings, in which.

DETAILED DESCRIPTION

Figure 1:
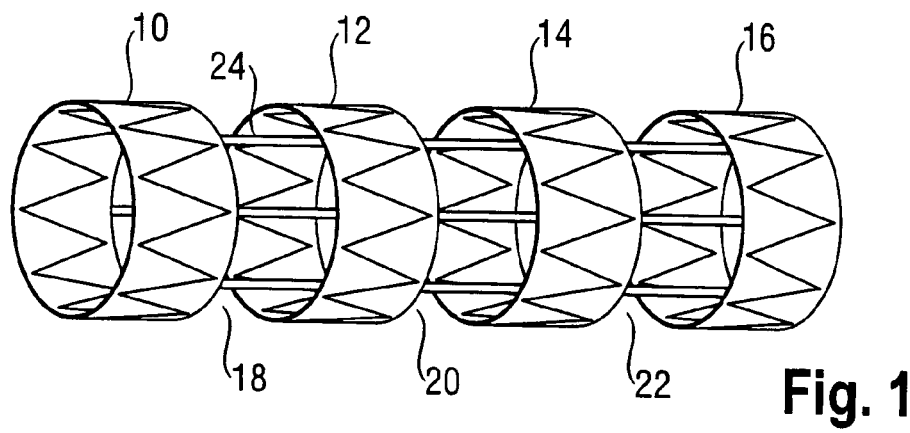
FIG. 1 is a side view of a first embodiment of polymer stent in accordance with the present invention.

Referring to FIG. 1, to be seen is a stent comprising four stenting segments 10, 12, 14 and 16 interspersed by linking segments 18, 20 and 22. Diagrammatically, the stenting segments are shown with a zigzag formation of struts that extends all around the circumference of the ring (as is well known in the stenting art). Within this art, there is a multitude of variations of the "zigzag" concept. Not only is there a multitude of strut and loop forms within the art but also a multitude of possibilities for bridging between adjacent zigzag form stenting rings, connecting adjacent loops, non-adjacent loops, loops to struts, struts to struts and so on, so as to create circumferentially staggered "peak-to-valley" adjacent rings, or non-staggered peak-to-peak rings. All of these many variations that have been developed in the technical field of stents are for consideration for applicability to the polymer of the present stenting rings. Metal stents are usually made from stainless steel, or tantalum, or nickel-titanium shape memory alloy, and are usually plastically deformable balloon expansible, elastically self-expanding, or martensitic/austenitic quasi-elastic self-expanding. Different expansion mechanisms have bred different stent matrix designs. Again, it should be pointed out here that polymer materials are so different from metals that in the present invention mesh cells and patterns as well as ways of making these cells and patterns, can be substantially different from the optimal arrangements for metal workpieces. What is preferred can depend on the medical application in view. The present polymer stents can lend themselves to medical applications not yet explored with metal stents, for example, applications that require time-dependent bio-absorptions of the stent.

Figure 2:
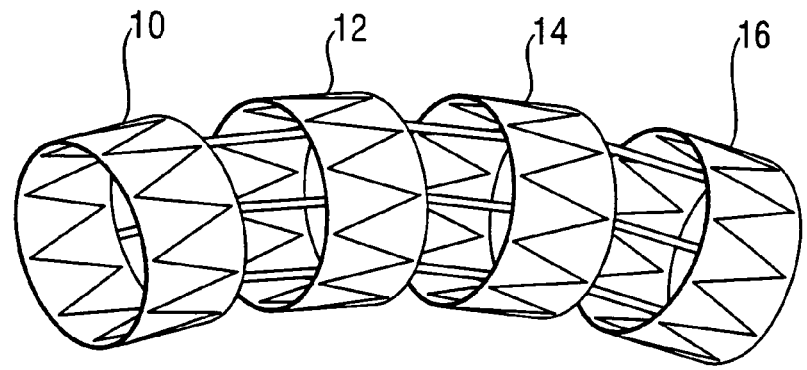
FIG. 2 is a similar sideways view of the FIG. 1 embodiment subject to bending stresses to the extent that it assumes a "banana" shape.

The linking segments are diagrammatically represented in FIG. 1 by a relatively small plurality of axially extending struts 24 distributed around the circumference of each linking segment at regular spaced intervals. This is only diagrammatic. In reality, the links are likely to be serpentine or to include some other non-axial component in order to provide the required capability to assume different axial lengths, to accommodate bending of the stent, as to be seen in the present FIG. 2. The links may also be cylindrical. Again, the published art of metal stents is replete with examples of linking strut shapes that allow bending of the stent and, again, it is the intention of the present inventor that all of these linking strut shapes should be available for consideration for their utility and providing the linking segments of the present invention.

Figure 3:
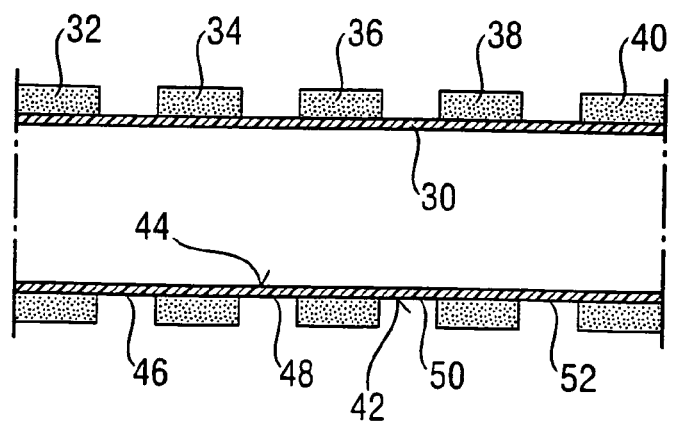
FIG. 3 is a longitudinal, diametrical section through a second embodiment of polymer stent in accordance with the present invention.
Figure 4A:
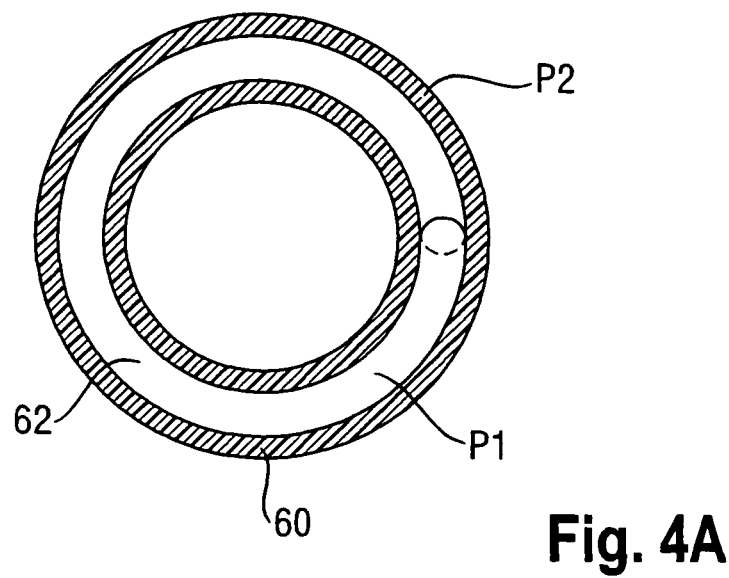
FIG. 4A is a transverse, diametrical section through a third embodiment of a polymer stent in accordance with the present invention.
Figure 4B:
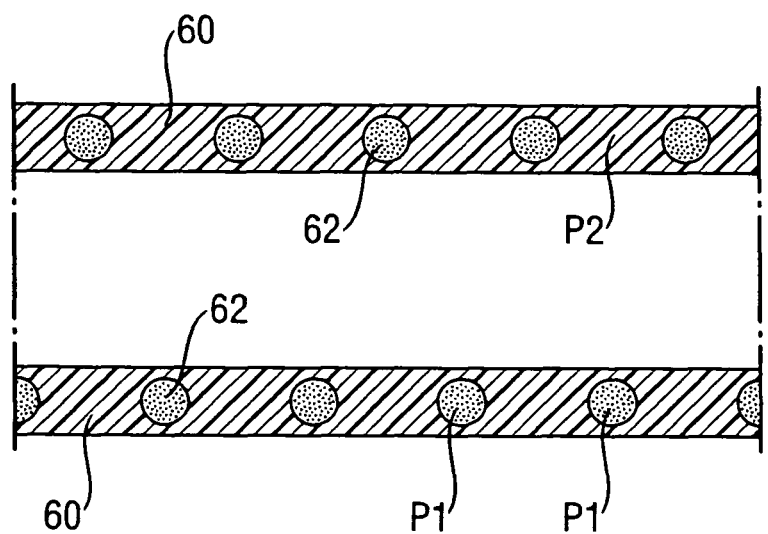
FIG. 4B is a longitudinal, diametrical section through a third embodiment of a polymer stent in accordance with the present invention.

Turning to FIG. 3, there is shown a polymer stent with a succession of five stenting segments 32 to 40 spaced along the length of the stent and bonded to the abluminal surface 42 of a tubular polymer component 30 that has a luminal surface 44. It is the tubular component 30 that provides the linking segments 46 to 52 that lie between adjacent pairs of stenting elements 32 to 40.

The tubular component 30 could be formed from a continuous-walled tube that has been apertured by, for example, chemical etching or laser cutting. Otherwise, the tube 30 could be created by braiding or weaving polymer fibers to create a tubular component with a multiplicity of through apertures.

Indeed, in a further embodiment, not illustrated, a woven or braided tube could be created with more than one type of polymer fiber, with the braiding pattern being modulated along the length of the tubular component to create alternate stenting segments and linking segments, hard and soft respectively, within the braiding pattern of the braided tube.

In another embodiment, not illustrated, a co-extrusion technique could be used to modulate the composition of a continuous extruded annular section, to create alternate hard and soft segments emerging from the annular extrusion die, with the extruded section subsequently being cut transversely into stent lengths containing a spaced plurality of stenting segments, with the stenting segments then being apertured by any appropriate technique such as laser cutting or chemical etching.

In a different co-extrusion technique, the additional of a rotational component to the extrusion of an annular profile, together with modulation of the composition of the extrudate around the circumference of the annular extrusion die, could create an annular extruded section that features a spiral of a relatively hard polymeric component destined to provide the stenting segments, and an adjacent spiral of a relatively softer polymeric component destined to provide the linking segments. Again, individual lengths of the extruded profile can be cut, with subsequent chemical etching or laser cutting or some other convenient technique being employed to aperture the workpiece in order to yield the necessary radial expandability of the stents of the present invention.

FIG. 4A-8B show schematically cross-sections of embodiments of a polymer prosthesis in accordance with the present invention. More in particular, FIG. 4A and FIG. 4B each show cross-sections of a third embodiment, wherein the polymer P1 of the relatively stiff stenting segments 62, is encapsulated between two layers of polymer P2 of the relatively flexible linking segments 60, which are in a form of two concentric layers of ePTFE.

Figure 5A:
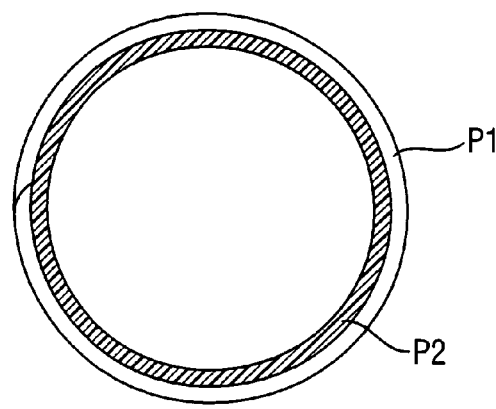
FIG. 5A is a transverse, diametrical section through a fourth embodiment of a polymer stent in accordance with the present invention.
Figure 5B:
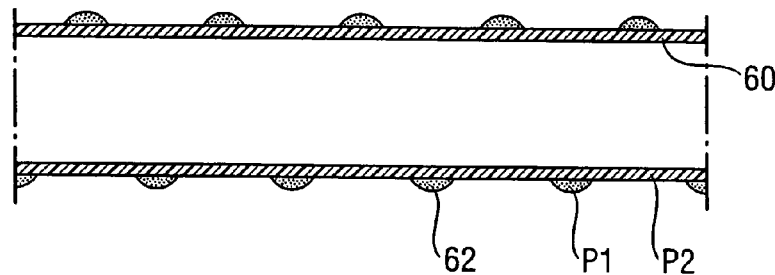
FIG. 5B is a longitudinal, diametrical section through the fourth embodiment of a polymer stent in accordance with the present invention.

FIGS. 5A and 5B each show cross-sections of a fourth embodiment, wherein the polymer P1 of the relatively stiff stenting segments 62 is positioned radially outwardly from the cylindrical component 60, acting here as the plurality of relatively flexible linking segment as portions of the continuous cylindrical component 60, which is preferably of ePTFE.

Figure 6A:
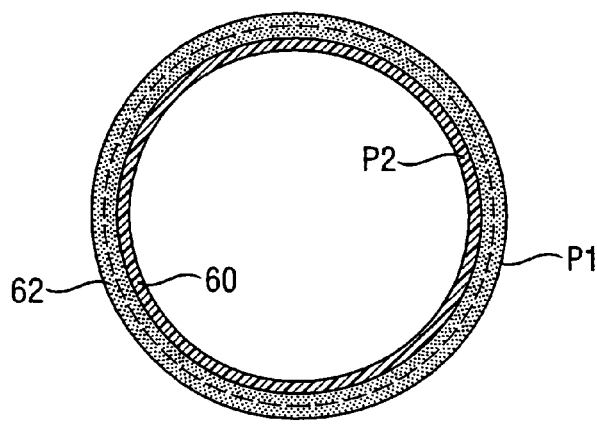
FIG. 6A is a transverse, diametrical section through a fifth embodiment of a polymer stent in accordance with the present invention.
Figure 6B:
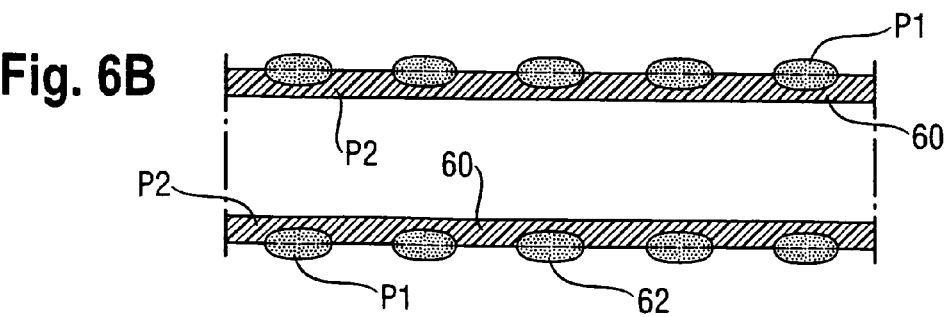
FIG. 6B is a longitudinal, diametrical section through the fifth embodiment of a polymer stent in accordance with the present invention.

FIG. 6A and FIG. 6B each show cross-sections of a fifth embodiment similar to the embodiment shown in FIGS. 5A and 5B. However, in FIGS. 6A and 6B the polymer P1 of the relatively stiff stenting segments is positioned at least partly within interstices formed in the polymer P2 of the plurality of relatively flexible linking segments, here again shown in the form of a continuous cylindrical component 60, preferably made of ePTFE.

Figure 7A:
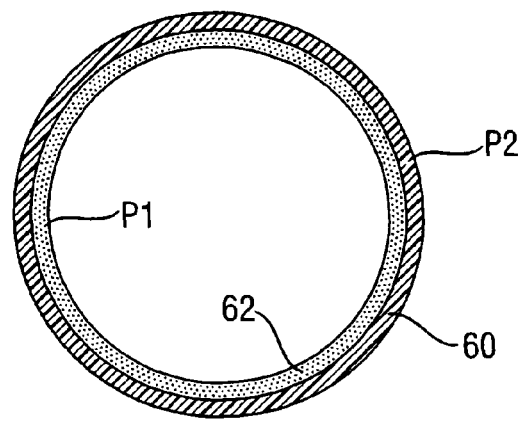
FIG. 7A is a transverse, diametrical section through a sixth embodiment of a polymer stent in accordance with the present invention.
Figure 7B:
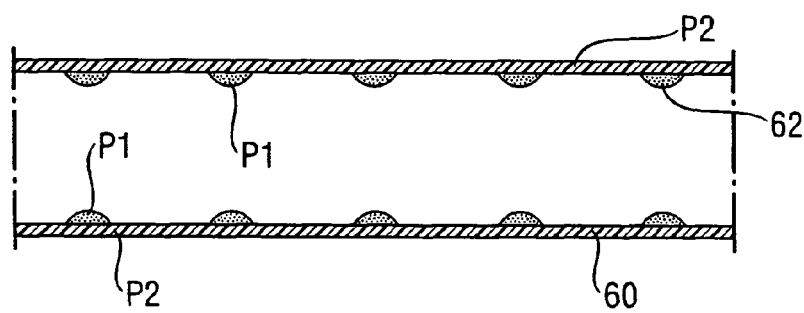
FIG. 7B is a longitudinal, diametrical section through a sixth embodiment of a polymer stent in accordance with the present invention.

FIG. 7A and FIG. 7B each show cross-sections of a sixth embodiment, wherein the polymer P1 of the relatively stiff stenting segment 62 is positioned substantially radially inwardly from the polymer P2 of the plurality of the relatively flexible linking segments, here again shown as portions of a continuous cylindrical component 60, which is preferably of ePTFE.

Figure 8A:
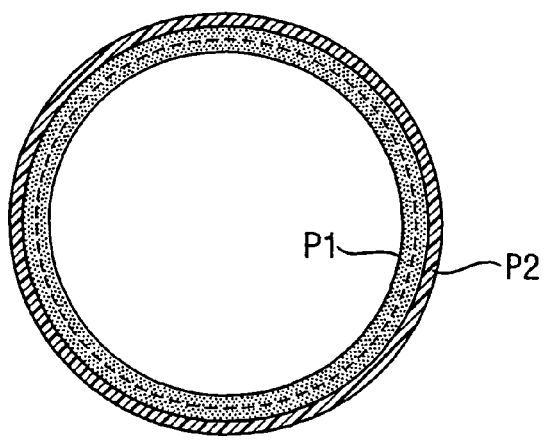
FIG. 8A is a transverse, diametrical section through an seventh embodiment of a polymer stent in accordance with the present invention.
Figure 8B:
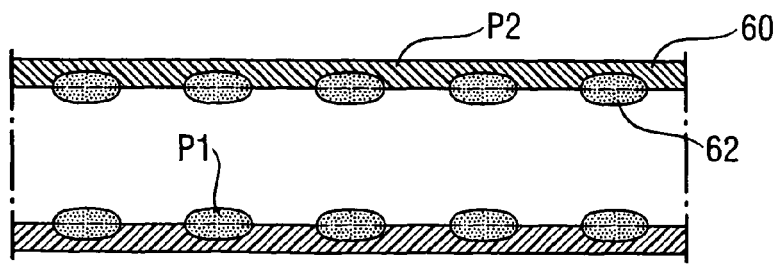
FIG. 8B is a transverse, diametrical section through an seventh embodiment of a polymer stent in accordance with the present invention.

FIG. 8A and FIG. 8B show schematically the cross sections of a seventh embodiment wherein the polymer P1 of the relatively stiff stenting segments 62 is positioned at least partly within interstices of the polymer P2, for example being ePTFE, and being provided in the form of a continuous cylindrical component 60. The polymer P1 is substantially radially inwardly positioned from the polymer P2. However, it is conceivable that the first polymer is occupying interstices throughout the thickness of the second polymer, i.e. throughout the thickness of the PTFE, from the outside to the inside.

Methods for forming the embodiments shown above, are now discussed.

Figure 9:
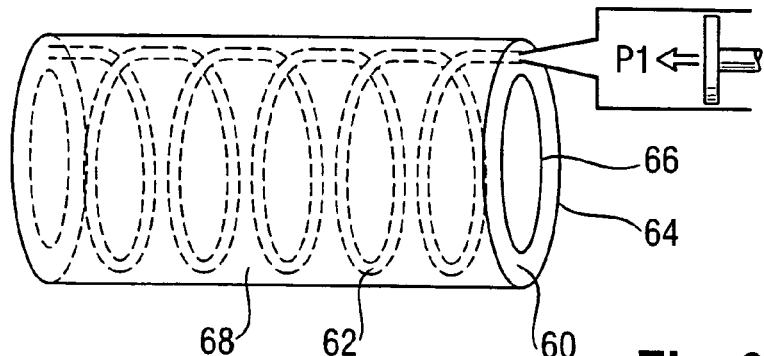
FIG. 9 schematically shows a possible way of forming the third embodiment of a polymer prosthesis according to the invention.

FIG. 9 shows schematically a possible way of forming the third embodiment of a polymer prosthesis according to the invention. A continuous cylindrical component 60, having the linking segments as portions thereof, carry the stenting segments 62. The continuous cylindrical component 60 is in the form of two concentric tubes 64, 66 bonded to each other at spaced intervals along the length of the tubes 64, 66 and around the circumferences. The embodiment shown in FIG. 9 is similar to the inflatable prosthesises as described in WO 2001/021107 and U.S. Pat. No. 5,156,620. The embodiment shown in FIG. 9 differs from the devices shown in the documents in that the embodiment according to the present invention not necessarily has a valve. However, it has an inflatable chamber 68 as formed between the bonded parts of the two concentric tubes 66, 64. In a method for forming a polymer prosthesis in accordance with the present invention is the inflatable chamber 68 injected with an injectable polymer in a stage which is prior to delivery of the polymer prosthesis in a body, in contrast to the injection taking place at the delivery site as described in the mentioned prior art documents. However, both U.S. Pat. No. 5,156,620 and WO 2001/021107 can be relied upon when a skilled practitioner wishes to produce an embodiment in analogy with the embodiment shown in FIG. 4.

Ideally, each end of the inflatable chamber 6, in FIG. 9 shown as a helix, is open on either end. However, it is also possible that one end is closed and that the air present in the inflatable chamber 68 prior to injection of a polymer, is forced out of the inflatable chamber 68 through the material of the concentric tubes 64, 66. This applies in particular when the cylindrical component 60 is made out of two concentric tubes 64, 66 which are each made of ePTFE.

In FIG. 9 is schematically shown how a second polymer P2 is injected into the inflatable chamber 68, thus forming the plurality of relatively stiff stenting segments by the hardening of polymer P1. A wide range of hardening or polymerisable liquids are available for use as the first polymer P1 and for injection into the inflatable chamber 68. Also various silicon rubbers, urethanes and other similar organic elastomers can be used. Polymerisable protein solutions are also very effective. Hydrophilic organic polymers (many being acrylate derivates) are know to gel or harden in response to a temperature increase. It is possible to inject such polymers in their liquid form below body temperature, i.e. outside the body, and have them hardened as they reach body temperature.

It will be understood that instead of injecting a polymer P1, it is also possible to insert a soft or softened flexible polymer wire into chamber 68. Once the chamber 68 has completely been occupied by that soft polymer wire, the polymer can be hardened by application of various well-known techniques which depend on the polymer used and which are generally well-known to the skilled practitioners. Various processes can be carried out to provide the polymer P1, forming the plurality of stenting segments, with a "memory", so that the polymer prosthesis can be radially compressed but will have a tendency driven by its "memory" to radially outward expand once being delivered to a delivery site in a body in a radially contracted condition. Reference is made to the list of documents mentioned in the introduction of the specification for polymers capable of having a memory, and to the list of polymers provided later on in this specification.

Figure 10:
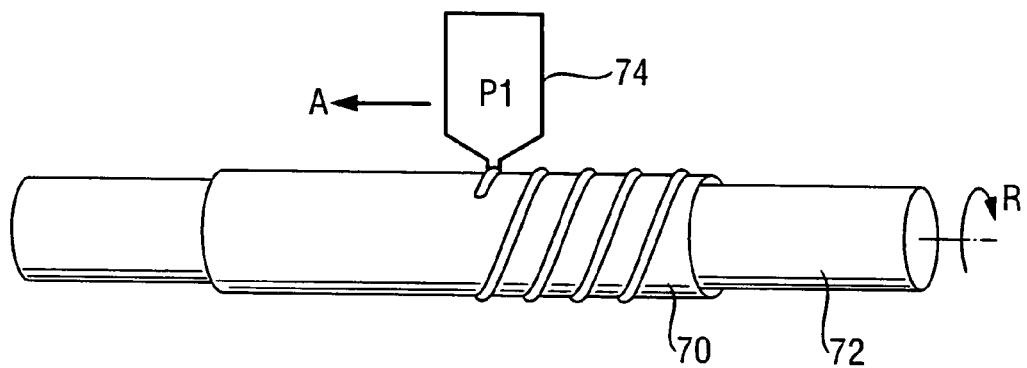
FIG. 10 schematically shows a possible way of forming the fourth embodiment of a polymer prosthesis according to the invention.

It is not inconceivable that the flexible linking segments comprise a shape-memory polymer in addition, or as an alternative, to the stenting segment provided with a "memory". FIG. 10 schematically shows a possible way of forming the fourth embodiment of a polymer prosthesis according to the invention. During this way of forming of a polymer prosthesis, use is again made of a continuous cylindrical component having the linking segments as portions thereof. In this case the continuous cylindrical component is a single cylindrical sheet/sheath 70, of a second polymer such as, for instance, ePTFE. This sheath 70 is coaxially placed around a mandrel 72 which can, for instance, rotate around its axis in the direction of arrow R. The first polymer P1 may flow out of a container 74 while this container is moving into the direction of arrow A. The viscosity of the polymer P1 flowing out of container 74 will be predetermined and such that the polymer P1 will fix to the polymer P2 of the single sheath 70. During this process as schematically outlined in FIG. 5, a plurality of relatively stiff stenting segments spaced from each other along the length of the prosthesis is formed upon hardening of the polymer P1. The stenting segments made of the first polymer P1 is being bridged by the plurality of a relatively flexible linking segment of the second polymer, in this case ePTFE.

Figure 11:
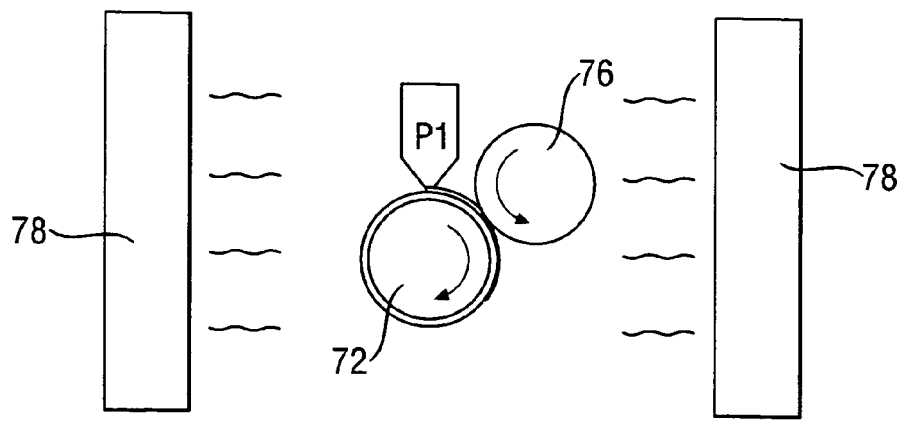
FIG. 11 schematically shows a possible way of forming the fifth embodiment of a polymer prosthesis according to the invention.

The polymer prosthesis as formed via a method schematically shown in FIG. 10, has the relatively stiff stenting segments arranged radially outward from the plurality of relatively flexible linking segments. Another method of making a polymer prosthesis with such a relative positioning of the stenting and linking segments is shown in FIG. 11 which shows schematically a view along the axis of the mandrel 72 shown in FIG. 10. In addition to the process outlined when discussing FIG. 10, a pressing roll 76 is applied to press the polymer P1 into interstices of the ePTFE, so that the stenting segments will occupy at least partly a number of selected interstices. FIG. 11 also shows elements 78 which could be either heating elements, or elements which provide, for instance, cold air, depending on what the fixation of the first polymer to the second polymer requires.

It will be clear that instead of applying a continuous spiral of polymer P1 to form the plurality of stiff stenting segments, it is also possible to interrupt the application of polymer P1 to the sheath 70 and continue further along the length of the cylindrical component 60 so that discrete rings of polymer P1, forming discrete stiff stenting segments, will be obtained. It will also be borne in mind that the outlined methods of forming an embodiment of a polymer prosthesis according to the invention, are preferably carried out such that the polymer prosthesis is formed in its radially expanded condition. It will further be understood that the continuous cylindrical component, forming the portions of linking segments may be held in an axially stretched or unstretched condition. The skilled practitioner will appreciate a large window of design parameters to end up with a polymer prosthesis within the concept of the invention.

Whilst FIG. 9 describes forming of, and discloses as such, a polymer prosthesis wherein the relatively stiff stenting segments are encapsulated by the relatively flexible linking segments, and FIGS. 10 and 11 show schematically the forming of, and as such the disclosure of, a polymer prosthesis having the relatively stiff stenting segments radially outward from the relatively flexible linking segments, it is also possible to form a polymer prosthesis having the relatively stiff stenting segments radially inward from the relatively flexible linking segments.

Figure 12:
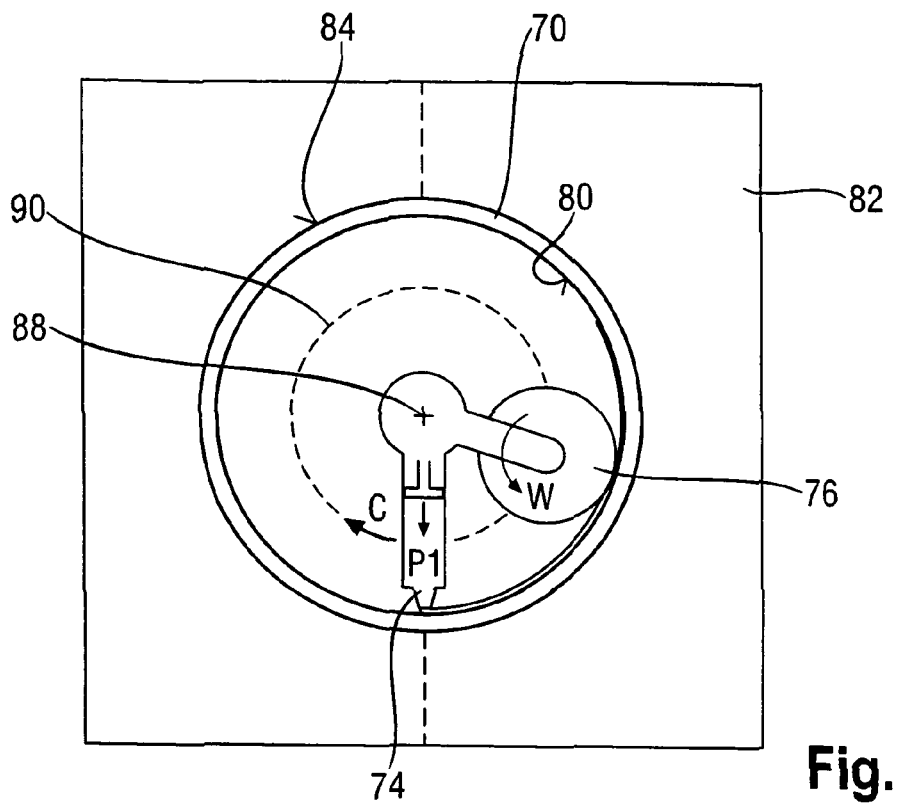
FIG. 12 schematically shows a possible way of forming the sixth and/or seventh embodiment of a polymer prosthesis according to the invention.
Figure 13:
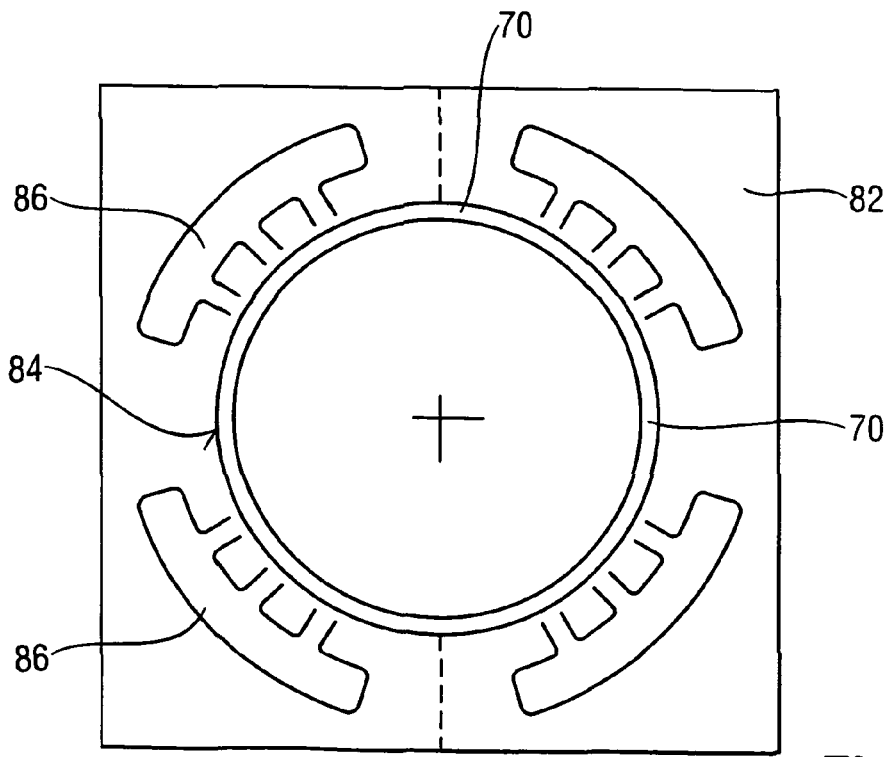
FIG. 13 schematically shows a part of a device that may be used for forming an embodiment of a polymer prosthesis according to the invention.

FIG. 12 shows schematically a method that is in a way a combination of the method shown in FIGS. 10 and 11. However, FIG. 12 shows how the polymer P1 is applied to the inner cylindrical wall 80 of the continuous cylindrical component 70. There is obviously no mandrel 72 and the cylindrical component 70 is fittingly held within, for instance, a two-part holder 82. The outer wall 84 of the cylindrical component 70 may be vacuum-clamped by the holder 82. Such clamps are schematically shown in FIG. 13 in which for the sake of clarity, the devices for the application of polymer P1 at the inner wall 80 of cylindrical components 70 is omitted. The holder 74 with polymer P1 is connected to an axis 88 and can rotate around the axis in a direction of arrow C. While doing so, the inner wall 80 of cylindrical component 70 is provided with polymer P1 for forming relatively stiff stenting segments. The pressing roll 76 can also rotate in the direction of arrow W whilst the pressing roll 76 itself describes a circular path schematically indicated by the dashed line 90.

Instead, or in addition to the pressing roll W, a drying or cooling device (not shown) may be applied. It will be clear that instead of rotating holder 74 and pressing roll 76, it is also possible to rotate instead, or additionally, cylindrical component 70 about its axis.

Again it applies that the polymer P1 may "describe" a helical path over the inner wall 80 of the cylindrical component 70, but it is also envisageable that discrete rings of polymer P1 are formed such that discrete rings of relatively stiff stenting segments are formed. Again it applies that the cylindrical component 70 may be in a stretched or unstretched condition, and again it applies that the polymer prosthesis may be formed as in a radially extended condition, depending on the other properties or treatments of the polymers.

Figure 14:
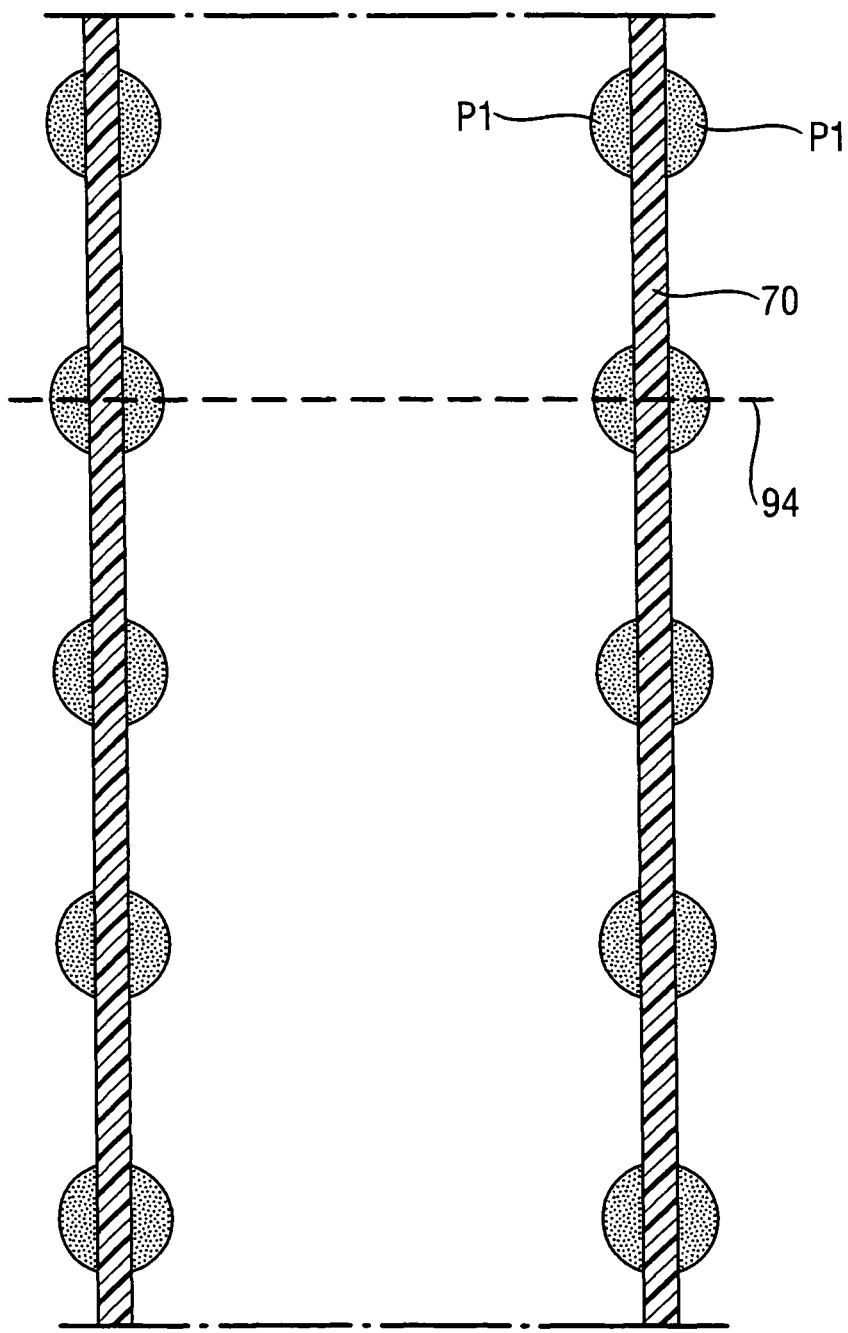
FIG. 14 schematically shows a cross-section of an eighth embodiment of a polymer prosthesis according to the invention.

FIG. 14 shows schematically a cross-section of a polymer prosthesis in which the relatively stiff stenting segments are positioned both radially inward and radially outward from the relatively flexible linking segments. The example of FIG. 14 shown as a continuous cylindrical component 70. As shown, it is possible that along the length of the polymer prosthesis one pair of a stenting segment positioned radially inward from the flexible linking segment and a stiff stenting segment positioned radially outward from the flexible linking segment, lie in one straight imaginary transverse plane, schematically indicated by dashed lines 94. However, it is also possible that the radially inwardly positioned stenting segments lie in transverse planes which are free from coinciding with radially outwardly positioned stenting segments.

An embodiment is shown in FIG. 14 which can of course be formed by sequentially applying methods shown in FIG. 10 and a method shown in FIG. 12. It is however also conceivable that the continuous cylindrical component 70 is clamped between a first substantially cylindrical stiff stenting segment having an outer diameter slightly larger than the inner diameter of the cylindrical component 70 and a second substantially cylindrical stiff stenting segment having a inner diameter that is slightly smaller than the outer diameter of the cylindrical component 70. Rather than mechanical clamping, various heat treatments may be applied to fuse the different polymers P1 and P2 together.

The invention is not limited to the examples and embodiments discussed above. Various modifications are possible.

The selective application of polymer P1 against or into polymer P2 may, for instance, also be possible by masking certain parts of polymer P2 so that polymer P1 can only be applied at unmasked portions of polymer P2. To obtain a polymer prosthesis that is as thin as one ePTFE sheath, it may be preferred that the polymer P1 is only applied within the interstices of ePTFE. Reference is made to WO 02/26279 indicating how an ePTFE sheath may be impregnated. In this document it is explained how a mandrel with pores can be used for impregnating a PTFE layer which is wrapped around a mandrel. For producing a polymer prosthesis in accordance with the present application, it is possible that a mandrel is selectively provided with pores which allow the first polymer to flow through the mandrel and to impregnate a PFTE tubular layer which is axially wrapped around the mandrel. Rather than, as discussed in the document, impregnating a foil with an encapsulated biologically active substance, the foil may in accordance with the present invention be impregnated with polymer P1 forming a relatively stiff stenting segment.

Although so far a number of possibilities of the relative radial positioning of the stenting segments and linking segments have been discussed hereinabove. The list of possibilities is not exhausted. It is also possible that a combination of these relative radial positionings is applied in a way similar over the entire length of the polymer prosthesis or in different ways over the entire length of the polymer prosthesis.

Figure 15:
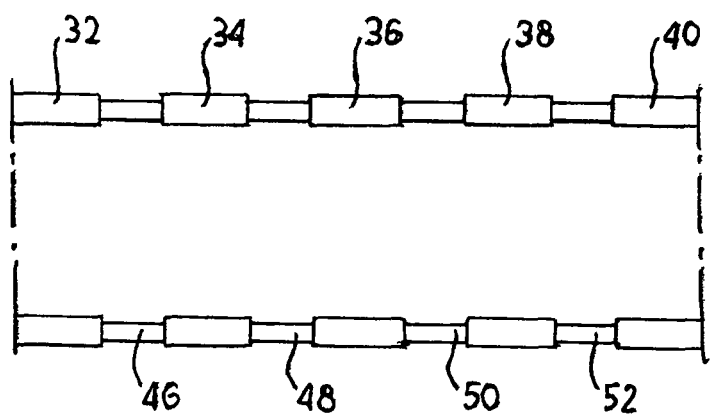
FIG. 15 schematically shows a cross section of a ninth embodiment of a polymer prosthesis according to the invention.

With reference to FIG. 15 it is further indicated that the flexible linking segment and the relatively stiff stenting segments may each have the shape of rings, preferably all of equal diameter and that the polymer prosthesis is formed by the formation of a single axis shared by all rings.

All such embodiments are understood to fall within the framework of the present invention as defined by the appended claims.

Bio-active agents can be added to the prosthesis (e.g., either by a coating or via a carrier medium such as resorbable polymers) for delivery to the host's vessel or duct. The bio-active agents may also be used to coat the entire stent. A material forming the stent or coupled to the stent may include one or more (a) non-genetic therapeutic agents, (b) genetic materials, (c) cells and combinations thereof with (d) other polymeric materials.

(a) Non-genetic therapeutic agents include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anticoagulants, an RGD peptide-containing compound, heparin, antithrombin compounds, platelet receptor antagonists, anti-thrombin anticodies, anti-platelet receptor antibodies, aspirin, prostaglandin inhibitors, platelet inhibitors and tick antiplatelet peptides; vascular cell growth promotors such as growth factor inhibitors, growth factor receptor antagonists, transcriptional activators, and translational promotors; vascular cell growth inhibitors such as growth factor inhibitors, growth factor receptor antagonists, transcriptional repressors, translational repressors, replication inhibitors, cell cycle inhibitors and activators, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms.

(b) Genetic materials include anti-sense DNA and anti-sense RNA as well as other molecules working via the same mechanism of transcriptional or translational inhibition or activation. Genetic material also include (sense) DNA or (sense) RNA or equivalents thereof coding for Genes to replace defective or deficient endogenous molecules or increase their amount or stability, or encode for non-endogenous or endogenous modified molecules with biological effects. Genetic material also includes nucleic acids affecting Gene expression or other cellular mechanisms by other ways than described above. Such Genetic materials could be organized "naked", packed with supporting molecules or in form of viruses or other vectors. Genes and their expression affected by above Genetic materials include but are not restricted to: tRNA or rRNA to replace defective or deficient endogenous molecules, angiogenic factors including growth factors such as acidic and basic fibroblast growth factors, vascular endothelial growth factor, epidermal growth factor, transforming growth factor alpha and beta, platelet-derived endothelial growth factor, platelet-derived growth factor, tumor necrosis factor alpha, hepatocyte growth factor and insulin like growth factor, cell cycle inhibitors and activators including CD inhibitors, thymidine kinase ("TK") and other agents useful for interfering with cell proliferation, transcription factors, translation factors, the family of bone morphogenic proteins ("BMP's"), BMP-2, BMP-3, BMP-4, BMP-5, BMP-6 (Vgr-1), BMP-7 (OP-1), BMP-8, BMP-9, BMP-10, BMP-1, BMP-12, BMP-13, BMP-14, BMP-15, and BMP-16. Desirable BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA''s encoding them.

(c) Cells can be of human origin (autologous or allogeneic) or from an animal source (xenogeneic), genetically engineered if desired to deliver proteins of interest at the deployment site. The cells may be provided in a delivery media. The delivery media may be formulated as needed to maintain cell function and viability.

(d) Suitable polymer materials as a coating or the base material may include polycarboxylic acids, cellulosic polymers, including cellulose acetate and cellulose nitrate, gelatin, polyvinylpyrrolidone, Cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, including cellulose, chitin, dextran, polyesters including polyethylene terephthalate, polyacrylamides, polyethers, polyether sulfone, polycarbonate, including tyrosine-derived polycarbonate, polyalkylenes including polypropylene, polyethylene and high molecular weight polyethylene and poly (butylenes terephthalate) (PBT), halogenated polyalkylenes including polytetrafluoroethylene, polyurethanes, polyorthoesters, proteins (including fibrin and casein), polypeptides, silicones, siloxane polymers, polylactic acid (PLA), polyglycolic acid (PGA), poly(lactide-co-glycolide) (PLGA), polycaprolactone, polydioxanone, poly(g-ethyl glutamate), poly(DTH iminocarbonate), poly(bisphenol A iminocarbonate), poly(ortho ester), polycyanoacrylate, and polyphosphazene, polyhydroxybutyrate valerate and blends and copolymers thereof, coatings from polymer dispersions such as polyurethane dispersions (for example, BAYHDROL® fibrin, collagen and derivatives thereof, polysaccharides such as celluloses, starches, dextrans, alginates and derivatives, hyaluronic acid, squalene emulsions. Polyacrylic acid, available as HYDROPLUS® (Boston Scientific Corporation, Natick, Mass.), and described in U.S. Pat. No. 5,091,205, the disclosure of which is hereby incorporated herein by reference, is particularly desirable. Even more desirable is a copolymer of polylactic acid and polycaprolactone.

INDUSTRIAL APPLICABILITY

It will be appreciated by the reader that the stents of the present invention are flexible for useful axial bending, not only in the delivery device but also, subsequently, after placement in the body. The stents have a good radial strength and force to keep patent the bodily lumen in which they are implanted, but also a strong measure of bending flexibility that will be a distinct advantage, especially in those applications where the bodily lumen in which the device is implanted is one that is required to undergo significant bending either in the course of transluminal delivery to that location or, after delivery, in the ordinary daily life of the patient in which the stent is implanted.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention.

Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

The invention claimed is:

1. A polymer prosthesis, comprising:
   a single generally tubular porous polymer member; and
   a plurality of relatively stiff stenting segments that are windings of a continuous helical member spaced apart along a longitudinal axis of the porous polymer member, the stenting segments formed of a polymer different from the polymer of the porous polymer member, each stenting segment disposed at least partially within interstices of the porous polymer member.

2. The prosthesis according to claim 1, wherein the stenting segments are positioned completely within the interstices of the porous polymer member.

3. The prosthesis according to claim 1, wherein a portion of each of the stenting segments is positioned radially outward from an outer surface of the porous polymer member.

4. The prosthesis according to claim 1, wherein a portion of each of the stenting segments is positioned radially inward from an inner surface of the porous polymer member.

5. The prosthesis according to claim 1, wherein the stenting segments are positioned both radially outward from an outer surface of the porous polymer member and radially inward from an inner surface of the porous polymer member.

6. The prosthesis according to claim 1, wherein each stenting segment includes an inner portion positioned radially inward from an inner surface of the porous polymer member and an outer portion positioned radially outward from an outer surface of the porous polymer member, the portion of the stenting segment between the inner portion and outer portion disposed within the interstices of the porous polymer member.

7. The prosthesis according to claim 1, wherein the polymer of the stenting segments is atomically different from the porous polymer member.

8. The prosthesis according to claim 1, wherein the polymer of the stenting segments has a glass transition temperature that is greater than 37° C.

9. The prosthesis according to claim 1, wherein the porous polymer member comprises expanded polytetrafluoroethylene.

10. The prosthesis according to claim 1, wherein the stenting segments comprise a shape memory polymer.

11. A method of making a polymer prosthesis, comprising:
    providing a single generally tubular porous polymer member;
    disposing a plurality of stenting segments comprising windings of a continuous spiral along a surface of the porous polymer member at spaced apart intervals, the stenting segments of the continuous spiral formed of a polymer different from the polymer of the porous polymer member and relatively stiff in relation thereto; and
    moving at least a portion of the stenting segments into interstices of the single porous polymer member.

12. The method according to claim 11, further comprising positioning the porous polymer member over a mandrel, wherein the moving step includes pressing the stenting segments through an outer surface of the porous polymer member into the interstices thereof.

13. The method according to claim 11, further comprising positioning the porous polymer member in a holding device such that an outer surface of the porous polymer member is engaged with one or more clamps, wherein the moving step includes pressing the stenting segments through an inner surface of the porous polymer member into the interstices thereof.

14. The method according to claim 11, further comprising the step of heating the stenting segments.

15. The method according to claim 11, further comprising the step of cooling the stenting segments.

16. A polymer prosthesis, comprising:
    a single generally tubular porous polymer member; and
    a plurality of relatively stiff stenting segments spaced apart along a longitudinal axis of the porous polymer member, the stenting segments formed of a polymer different from the polymer of the porous polymer member, each stenting segment disposed at least partially within interstices of the porous polymer member such that an inner portion of the stenting segment is positioned radially inward from an inner surface of the porous polymer member and an outer portion of the stenting segment is positioned radially outward from an outer surface of the porous polymer member, the portion of the stenting segment between the inner portion and the outer portion being disposed within the interstices of the porous polymer member.

17. A polymer prosthesis, comprising:
    a single generally tubular porous polymer member; and
    a plurality of relatively stiff stenting segments that are discrete rings spaced apart along a longitudinal axis of the porous polymer member, the stenting segments formed of a polymer different from the polymer of the porous polymer member, each stenting segment disposed at least partially within interstices of the porous polymer member.

18. The prosthesis according to claim 17, wherein the stenting segments are positioned completely within the interstices of the porous polymer member.

19. The prosthesis according to claim 17, wherein a portion of each of the stenting segments is positioned radially outward from an outer surface of the porous polymer member.

20. The prosthesis according to claim 17, wherein a portion of each of the stenting segments is positioned radially inward from an inner surface of the porous polymer member.

21. The prosthesis according to claim 17, wherein the stenting segments are positioned both radially outward from an outer surface of the porous polymer member and radially inward from an inner surface of the porous polymer member.

22. The prosthesis according to claim 17, wherein each stenting segment includes an inner portion positioned radially inward from an inner surface of the porous polymer member and an outer portion positioned radially outward from an outer surface of the porous polymer member, the portion of the stenting segment between the inner portion and outer portion disposed within the interstices of the porous polymer member.

23. The prosthesis according to claim 17, wherein the polymer of the stenting segments is atomically different from the porous polymer member.

24. The prosthesis according to claim 17, wherein the polymer of the stenting segments has a glass transition temperature that is greater than 37° C.

25. The prosthesis according to claim 17, wherein the porous polymer member comprises expanded polytetrafluoroethylene.

26. The prosthesis according to claim 17, wherein the stenting segments comprise a shape memory polymer.

27. A method of making a polymer prosthesis, comprising:
providing a single generally tubular porous polymer member;
disposing a plurality of stenting segments along a surface of the porous polymer member at spaced apart intervals, the stenting segments formed of a polymer different from the polymer of the porous polymer member and relatively stiff in relation thereto;
positioning the porous polymer member in a holding device such that an outer surface of the porous polymer member is engaged with one or more clamps; and
moving at least a portion of the stenting segments into interstices of the single porous polymer member by pressing the stenting segments through an inner surface of the porous polymer member.

28. A method of making a polymer prosthesis, comprising:
providing a single generally tubular porous polymer member;
disposing a plurality of stenting segments comprising discrete rings along a surface of the porous polymer member at spaced apart intervals, the stenting segments formed of a polymer different from the polymer of the porous polymer member and relatively stiff in relation thereto; and
moving at least a portion of the stenting segments into interstices of the single porous polymer member.

29. The method according to claim 28, further comprising positioning the porous polymer member over a mandrel, wherein the moving step includes pressing the stenting segments through an outer surface of the porous polymer member into the interstices thereof.

30. The method according to claim 28, further comprising positioning the porous polymer member in a holding device such that an outer surface of the porous polymer member is engaged with one or more clamps, wherein the moving step includes pressing the stenting segments through an inner surface of the porous polymer member into the interstices thereof.

31. The method according to claim 28, further comprising the step of heating the stenting segments.

32. The method according to claim 28, further comprising the step of cooling the stenting segments.

* * * * *